United States Patent
Kapre et al.

(10) Patent No.: US 11,389,519 B2
(45) Date of Patent: Jul. 19, 2022

(54) VIRUS-LIKE PARTICLE CONJUGATES

(71) Applicant: Inventprise, LLC, Redmond, WA (US)

(72) Inventors: Subhash V. Kapre, Redmond, WA (US); Anup K. Datta, Renton, WA (US)

(73) Assignee: Inventprise, LLC, Redmond, WA (US)

( * ) Notice: Subject to any disclaimer, the term of this patent is extended or adjusted under 35 U.S.C. 154(b) by 0 days.

(21) Appl. No.: 16/435,502

(22) Filed: Jun. 9, 2019

(65) Prior Publication Data

US 2019/0374630 A1 Dec. 12, 2019

Related U.S. Application Data

(60) Provisional application No. 62/683,787, filed on Jun. 12, 2018, provisional application No. 62/683,543, filed on Jun. 11, 2018.

(51) Int. Cl.
  *A61K 39/108* (2006.01)
  *A61K 39/12* (2006.01)
  *C07K 14/025* (2006.01)
  *A61K 39/39* (2006.01)
  *C12N 7/00* (2006.01)
  *A61K 47/65* (2017.01)

(52) U.S. Cl.
  CPC .......... *A61K 39/0258* (2013.01); *A61K 39/12* (2013.01); *A61K 39/39* (2013.01); *A61K 47/65* (2017.08); *C07K 14/025* (2013.01); *C12N 7/00* (2013.01); *C12N 2710/20023* (2013.01)

(58) Field of Classification Search
  None
  See application file for complete search history.

(56) References Cited

U.S. PATENT DOCUMENTS

| | | | |
|---|---|---|---|
| 2012/0308592 A1 | 12/2012 | Chackerian et al. | |
| 2013/0331548 A1 | 12/2013 | Nakaar et al. | |
| 2017/0095577 A1* | 4/2017 | Woodard | A61K 49/0032 |
| 2018/0169262 A1* | 6/2018 | Lu | A61K 47/6817 |

FOREIGN PATENT DOCUMENTS

| | | |
|---|---|---|
| CN | 102747047 | 10/2012 |
| WO | WO2012/177970 | 12/2012 |

OTHER PUBLICATIONS

Roberts MJ, Bentley MD, Harris JM. Chemistry for peptide and protein PEGylation. Adv Drug Deliv Rev. Jun. 17, 2002;54(4):459-76. doi: 10.1016/s0169-409x(02)00022-4. PMID: 12052709. (Year: 2002).*

Wang JW, Roden RB. Virus-like particles for the prevention of human papillomavirus-associated malignancies. Expert Rev Vaccines. Feb. 2013;12(2):129-41. doi: 10.1586/erv.12.151. PMID: 23414405; PMCID: PMC3835148. (Year: 2013).*

International Search Report and Opinion for PCT/US2019/36243 dated Aug. 28, 2019.

(Continued)

*Primary Examiner* — Michelle S Horning
(74) *Attorney, Agent, or Firm* — Remenick PLLC

(57) ABSTRACT

This invention is directed to immunogenic composition, conjugates, virus-lie particles (VLP) compositions, vaccines and methods directed to the treatment and/or prevent of infection by Human Papillomavirus.

30 Claims, 3 Drawing Sheets

HPV VLPL1 16-CRM197-VLP L1 Conjugate

HPV VLP L1-16-CRM197 Conjugate

S-CRM197 -COOH Aspartic or Glutamic acid

HPV VLP L1 18-free amine

HPV VLP L1 16

S-CRM197 —— CO-NH

HPV VLP L1-18

(56) References Cited

OTHER PUBLICATIONS

Schellenbacher et al., Chimeric L1-L2 Virus-Like Particles as Potential Broad-Spectrum Human Papillomavirus Vaccines, Journal of Virology 83(19):10085-10095 (Sep. 8, 2009).
Examination report for AU Application No. 2019/287443 dated Apr. 4, 2022.
Examination Report for JP Application No. 2020-568688 dated Mar. 1, 2022.
Examination Report for JP Application No. 2020-568688 dated Mar. 1, 2022 (translated).
Examination report for ID Application No. P00202009616 dated May 23, 2022.
Examination report for ID Application No. P00202009616 dated May 23, 2022 (translated).

* cited by examiner

Figure 1

| Linker Structure | Chemical Structures/KD or Å used |
|---|---|
| 1. NH2-PEG-NH2/NHS | $H_2N-(CH_2CH_2O)_n-CH_2CH_2-NH_2$<br>1K and 3.5K |
| 2. NHS/NH2-PEG-COOH | $H_2N-CH_2CH_2-PEG-\overset{O}{\underset{\|}{C}}-OH$<br>1K and 3.5K |
| 3. Mal-PEG-NH2 | Maleimide-$CH_2CH_2\overset{O}{\underset{\|}{C}}-NH[CH_2CH_2O]_nCH_2-NH_2$<br>1K and 3.5K |
| 4. Mal-PEG-NHS | Maleimide-$CH_2CH_2-PEG-\overset{O}{\underset{\|}{C}}-O-N$(succinimidyl)<br>1K and 3.5K |
| 5. SH-PEG-NH2 | $HS-(CH_2CH_2O)_n-CH_2CH_2-NH_2$<br>1K and 3.5K |
| 6. ADH | $H_2N-\overset{H}{\underset{\|}{N}}-\overset{O}{\underset{\|}{C}}-(CH_2)_4-\overset{O}{\underset{\|}{C}}-\overset{H}{\underset{\|}{N}}-NH_2$ |
| 7. HZ-PEG-HZ | $NH_2NH\overset{O}{\underset{\|}{C}}CH_2O(CH_2CH_2O)_nCH_2\overset{O}{\underset{\|}{C}}NHNH_2$<br>Hydrazide-PEG-Hydrazide<br>1K and 3K |
| 8. 2-Imino-thilane | 2-iminothiolane · HCl |
| 9. SMPH | SMPH<br>Succinimidyl 6-[(β-maleimidopropionamido)hexanoate]<br>MW 379.36<br>Spacer Arm 14.2 Å |
| 10. SH-PEG-COOH | $HS-CH_2CH_2-[O-CH_2CH_2]_n-O-\overset{O}{\underset{\|}{C}}-OH$<br>1K and 3K |

Figure 2
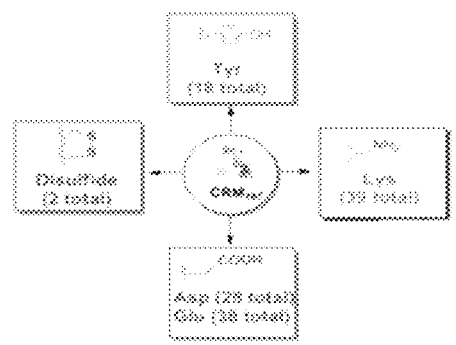
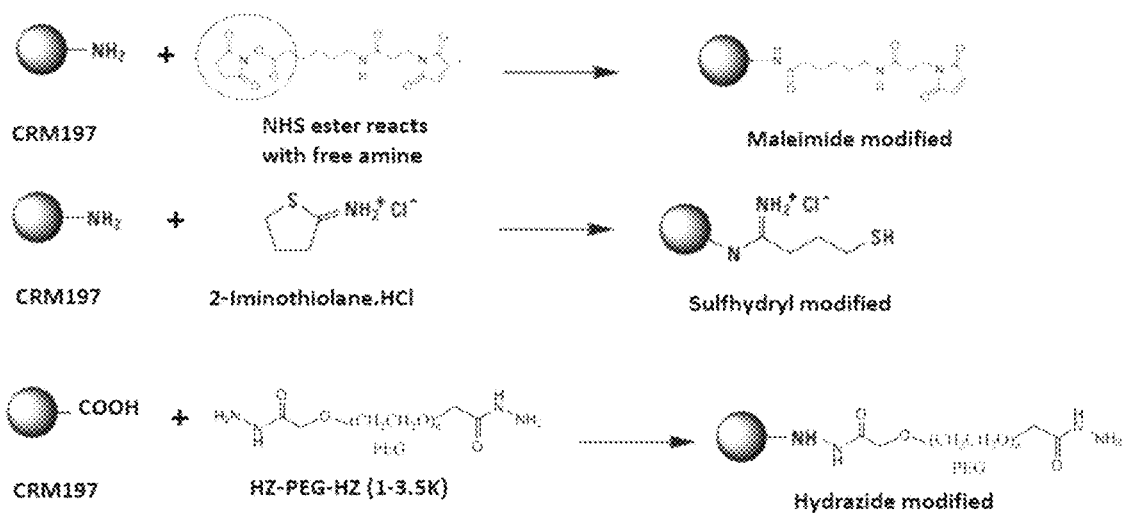

Figure 3

Activation of HPV VLP

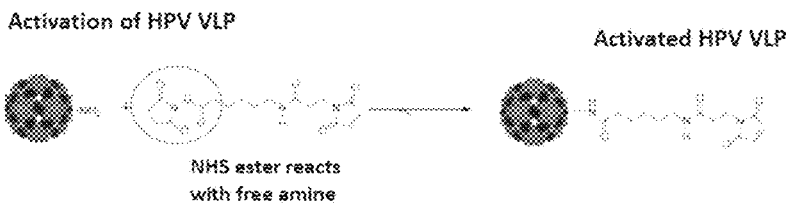

Activated HPV VLP

NHS ester reacts with free amine

Thiolation of CRM197 with Iminothiolene

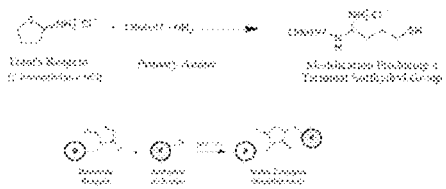

Conjugation with Thiolated CRM197 (SH-CRM197)

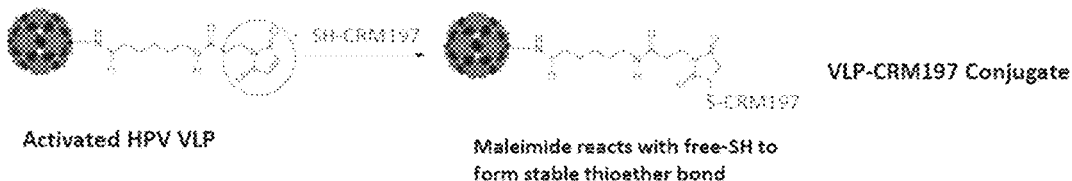

VLP-CRM197 Conjugate

Activated HPV VLP

Maleimide reacts with free-SH to form stable thioether bond

Figure 4

HPV VLPL1 16-CRM197-VLP L1 Conjugate

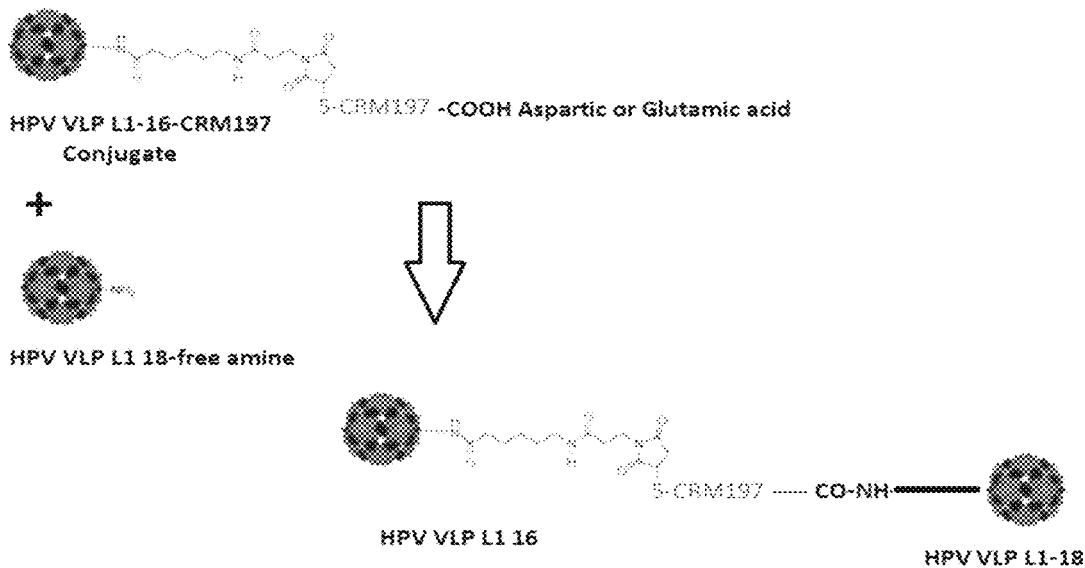

HPV VLP L1-16-CRM197 Conjugate   -COOH Aspartic or Glutamic acid

+

HPV VLP L1 18-free amine

HPV VLP L1 16

HPV VLP L1-18

VIRUS-LIKE PARTICLE CONJUGATES

REFERENCE TO RELATED APPLICATIONS

This application claims priority to U.S. Provisional Application No. 62/683,787 filed Jun. 12, 2018, and U.S. Provisional Application No. 62/683,543 filed Jun. 11, 2018, the entirety of each of which is incorporated by reference.

BACKGROUND OF THE INVENTION

1. Field of the Invention

This invention is directed to immunogenic composition, conjugates, virus-like particles (VLP) compositions, vaccines and methods directed to the treatment and/or prevent of infection by Human Papillomavirus.

2. Description of the Background

Human Papillomavirus (HPV) is a double stranded DNA virus, which targets the basal cells of squamous epithelia for infection. HPV's circular DNA genome is composed of two major oncogenes, E6 and E7, and two major structural protein genes, L1 and L2. Most conventional vaccines are developed based on these components. The L1 protein of HPV expressed recombinantly in vitro self-assembles into virus-like particles (VLPs). VLPs have HPV type-specific conformational neutralizing epitopes and are used for the development of VLP-based vaccine products. Typically, VLPs are recombinantly expressed in yeast, bacterial, or insect cell expression systems.

Two HPV vaccines are currently on the market, Gardasil (Merck and Co. Inc.) and Cervarix (GSK). The composition and dose of the Gardasil vaccine comprises HPV VLP L1 protein containing 6, 11, 16, 18, 1, 33, 45, 52, 58, a total of 9-serotypes and an aluminum adjuvant. The VLPs are present in an amount of 20-40 µg each per dose. The vaccine is administered as a 3-dose regimen according to a 0, 2, and 6-month schedule. The Cervarix vaccine comprises HPV VLPs 16 and 18 L1 proteins, and an adjuvant containing aluminum hydroxide and MPLA (3D-MPL). The VLPs are present at 20 µg each per dose. This vaccine is also administered as a 3-dose regimen according to a 0, 2, and 6-month schedule.

The cost of vaccine and the number of doses remain a main block in immunizing the population in developing world. Thus, a lower cost and lower dose vaccine is in great need throughout the world.

SUMMARY OF THE INVENTION

The present invention overcomes the problems and disadvantages associated with current strategies and designs and provides new immunogenic compositions, method of manufacturing immunogenic compositions, and methods of treated and preventing infections with the immunogenic compositions.

One embodiment of the invention is directed to immunogenic compositions such as a vaccine comprising virus-like particles (VLPs) obtained or derived from L1 and/or L2 proteins of Human papilloma virus (HPV), conjugated with a spacer arm and a carrier protein. Preferably the HPV comprises serotype 6, 11, 16, 18, 31, 33, 45, 52, and/or 58. Preferably the spacer arm comprises a hetero- or homo-bifunctional or multifunctional spacer arm, or in particular, comprises $NH_2$-PEG-$NH_2$/NHS, NHS/$NH_2$-PEG-COOH, Mal-PEG-$NH_2$, Mal-PEG-NHS, CHO-PEG-CHO, SH-PEG-$NH_2$, ADH, HZ-PEG-HZ, SMPH, SMCC, 4-Arm-PEG-$NH_2$. Preferably the carrier protein comprises tetanus toxoid, diphtheria toxoid, CRM197, tetanus toxoid fragments (TTHc), *N. meningitidis* protein PorB, RSV virus proteins, *B. pertussis* proteins, Pertussis toxoid (PT), adenylate cyclase toxin (ACT), 69 KDa protein, Human Papilloma viral protein antigens, Human Papilloma virus VLP forms, Hepatitis B virus core antigen, Hepatitis B virus VLP forms, derivatives of HBsAg, and/or combinations thereof. Preferably the immunogenic composition comprises an adjuvant, and preferably the adjuvant comprises aluminum salt, calcium phosphate, a liposome of monophosphoryl lipid A (MPLA), saponin QS-21, TLR ligands, and/or a potent TLR4/7/8/9 agonists. Preferred aluminum salts include one or more of aluminum phosphate, aluminum sulfate and/or aluminum hydroxide. Preferably the immunogenic composition, when administered to a patient, boosts the efficacy of a conventional vaccine.

Another and related embodiment of the invention comprises an immunogenic composition as described herein wherein the VLP is obtained or derived from HPV L1 protein or HPV L2 protein and the carrier protein is CRM197.

Another and related embodiment of the invention comprises an immunogenic composition as described herein wherein the VLPs are bi-valent L1 VLP conjugates, the HPV is serotype 16 and/or 18, and the carrier protein is CRM197.

Another and related embodiment of the invention comprises an immunogenic composition as described herein wherein the VLPs are bi-valent L1 VLP conjugates, the HPV is serotype 6 and/or 11, and the carrier protein is CRM197.

Another and related embodiment of the invention comprises an immunogenic composition as described herein wherein the VLPs are bi-valent L1 VLP conjugates, the HPV is serotype 31 and/or 33, and the carrier protein is CRM197.

Another and related embodiment of the invention comprises an immunogenic composition as described herein wherein the VLPs are bi-valent L1 VLP conjugates, the HPV is serotype 45 and/or 52, and the carrier protein is CRM197.

Another and related embodiment of the invention comprises an immunogenic composition as described herein wherein the VLPs are bi-valent L1 VLP conjugates, the HPV is serotype 58, and the carrier protein is CRM197.

Another and related embodiment of the invention comprises an immunogenic composition as described herein wherein the VLPs comprise L1 protein conjugated to L2 protein, and the carrier protein is CRM197.

Another and related embodiment of the invention comprises the process of manufacturing and using the immunogenic compositions of the disclosure. Preferably the immunogenic compositions and stable and provide protection against infections at lower doses or less frequently than are available using conventional immunogenic compositions.

Other embodiments and advantages of the invention are set forth in part in the description, which follows, and in part, may be obvious from this description, or may be learned from the practice of the invention.

DESCRIPTION OF THE FIGURES

FIG. 1 Bi-functional spacer arm for activation of CRM197: Mal-Maleimide, NHS-Succinimide, PEG-Polyethylene glycol derivatives, ADH-Adipic acid di-hydrazide, HZ-hydrazide, 1 k and 3K-Mn 1000 and 3500.

FIG. 2 Schematic of the mechanism of action of VLP.

FIG. 3 Schematic of conjugation of VLP with carrier protein CRM197 with a spacer arm.

FIG. 4 Schematic of VLP-CRM-VLP conjugate, where HPV VLP L116 type is first conjugates according to scheme 2, followed by VLP L1 18 type is conjugated with VLP L1-CRM197 conjugate.

DESCRIPTION OF THE INVENTION

It was surprisingly discovered that a conjugate could be made that provides HPV immunity equivalent to conventional HPV vaccines and with only two doses and with reduced antigens per dose making. The consequence is a vaccine that is five-fold less expensive than conventional vaccines and requires a lower dose making the vaccine more practical and more widely available.

The disclosure is directed to a pharmaceutical conjugate vaccine composition for a human cervical cancer, comprising of virus-like particles preferably derived from L1 HPV clones, conjugated using a spacer arm with a carrier protein, preferably CRM197 and CRM197-like proteins, used in conjugate vaccines and one L2-HPV VLP, and a pharmaceutically acceptable aluminum adjuvant (or non-aluminum adjuvant) and suitable buffer. The conjugate combination comprises combination of L1 and L2 VLPs for the regions where the prevalent infections of those serotypes exist.

The disclosure is directed to immunogenic compositions comprising virus-like particles (VLPs) obtained or derived from L1 and/or L2 proteins of Human papilloma virus (HPV), conjugated with a spacer arm and a carrier protein. Preferably the HPV comprises serotype 6, 11, 16, 18, 31, 33, 45, 52, and/or 58. Preferably the spacer arm comprises a hetero- or homo-bifunctional or multifunctional spacer arm, or in particular, comprises $NH_2$-PEG-$NH_2$/NHS, NHS/$NH_2$-PEG-COOH, Mal-PEG-$NH_2$, Mal-PEG-NHS, CHO-PEG-CHO, SH-PEG-$NH_2$, ADH, HZ-PEG-HZ, SMPH, SMCC, 4-Arm-PEG-$NH_2$. Preferably the carrier protein comprises tetanus toxoid, diphtheria toxoid, CRM197, tetanus toxoid fragments (TTHc), N. meningitidis protein PorB, RSV virus proteins, B. pertussis proteins, Pertussis toxoid (PT), adenylate cyclase toxin (ACT), 69 KDa protein, Human Papilloma viral protein antigens, Human Papilloma virus VLP forms, Hepatitis B virus core antigen, Hepatitis B virus VLP forms, derivatives of HBsAg, and/or combinations thereof. Preferably the immunogenic composition comprises an adjuvant, and preferably the adjuvant comprises aluminum salt, calcium phosphate, a liposome of monophosphoryl lipid A (MPLA), saponin QS-21, TLR ligands, and/or a potent TLR4/7/8/9 agonists. Preferred aluminum salts include one or more of aluminum phosphate, aluminum sulfate and/or aluminum hydroxide. Preferably the immunogenic composition, when administered to a patient, boosts the efficacy of a conventional vaccine.

This disclosure comprises an immunogenic composition as described herein wherein the VLP is obtained or derived from HPV L1 protein or HPV L2 protein and the carrier protein is CRM197; wherein the VLPs are bi-valent L1 VLP conjugates, the HPV is serotype 16 and/or 18, and the carrier protein is CRM197; wherein the VLPs are bi-valent L1 VLP conjugates, the HPV is serotype 6 and/or 11, and the carrier protein is CRM197; wherein the VLPs are bi-valent L1 VLP conjugates, the HPV is serotype 31 and/or 33, and the carrier protein is CRM197; wherein the VLPs are bi-valent L1 VLP conjugates, the HPV is serotype 45 and/or 52, and the carrier protein is CRM197; wherein the VLPs are bi-valent L1 VLP conjugates, the HPV is serotype 58, and the carrier protein is CRM197; and wherein the VLPs comprise L1 protein conjugated to L2 protein, and the carrier protein is CRM197.

The present disclosure includes formulation for at least 9-, 10- or higher valent VLP conjugate vaccine which reduces the necessary dose (8-10 µg/dose of individual VLPs compared with 20-40 µg dose used in Gardasil, Merck or Cerverix, GSK) adsorbed in aluminum phosphate or aluminum hydroxide or other suitable TLR7/8/9 or TLR 4 adjuvants. Examples of VLP-protein conjugates formulations:

VLP1-CRM197-VLP2 (4 and 9-valent L1, 10-valent with L2);
HPV-VLP/CRM197 (monovalent conjugates); and
VLP1-CRM197-VLP2 (4 and 9-valent L1, 10-valent with L2).

Conjugates include conjugation with HBHBSAg as, for example, HBSAg-VLP/CRM197.

The present disclosure is directed to L1 VLP-based 9 valent vaccine candidates as well as addition of L2-VLP based 10 valent vaccines. Four sets of two L1 VLPs are chemically conjugated using a bi-functional spacer arm with a carrier protein (e.g., CRM197 from E. coli) and one L1-VLPs conjugated with L2 VLP. L1 and L2-based VLP conjugates can be in general structurally represented as:

L1-XX-VLP-spacer arm-CRM197 L1-XX-VLP
L1-XX-VLP-spacer arm-CRM197 L2-VLP
XX can be any L1 VLP
Examples included are,
L1 VLP16-Spacer arm-CRM197-L1 VLP18
L1 VLP6-spacer arm-CRM197-L1 VLP11
L1 VLP31-spacer arm-CRM197-L1 VLP33
L1 VLP45-spacer arm-CRM197-L1 VLP52
L1 VLP58-spacer arm-CRM197-L2 VLP The following examples illustrate embodiments of the invention but should not be viewed as limiting the scope of the invention.

EXAMPLES

Example 1: Expression and Purification of Recombinant HPV L1 and L2 VLP in Yeast L1 protein from all 9 serotypes and L2 protein are expressed in Yeast Hansenula polymorpha. Fermentation cycle: 120 hrs. Expression induced by Methanol using H.P. promoter. The L1 and L2 protein were extracted using yeast cell wall lytic enzymes Zymolase, followed by Benzonase treatment for nucleic acid removal. The extraction step was carried out in TRIS buffer, 20-50 mM, pH 8.5-9.5. The clarified extract (concentration 1 mg/ml, with the L1 protein 150-200 ug/ml), were applied to a cation-exchange chromatography, followed by gel filtration chromatography. In this step, the di-assembly was utilized and assemble step causing the VLP's to assemble in the right configuration and stable molecules. This is confirmed using TEM, The VLPs were stabilized using appropriate buffer. Finally, VLPS are Concentrated using ultrafiltration.

All serotypes L1 VLPs and L2 VLP purification yields are in the region of 7-15% of cell extract, the purified VLPs are 98-99% homogeneous purity. FIG. 2 describes the process flow chart showing the experimental procedures used to purify L1 and L2 HPV serotypes VLPs. All purified VLPs were checked for amino acid sequence, free thiols and lysine's are used with the purpose of stability and site availability for chemical conjugation with carrier proteins.

Example 2. Chemical Conjugation Procedure of L1 and L2 VLPs with CRM197

Chemical conjugation of VLPs are accomplished by the use of chemical cross-linkers, moreover, various conjugation strategies used, for example, use pegylated homo or hetero-bifunctional conjugation reagents having same or two evident reactive groups which can bond to different and distinct functional targets, one on the antigen and the other on the VLP (typically amines or sulfhydryl residues).

Example 3. Activation of CRM197 Using Bi-Functional Spacer Arm

Carrier protein CRM197 activation using pegylated and non-homo or hetero-bifunctional spacer arm. CRM-197 (10 mg/ml) was dissolved in activation buffer, followed by bi-functional spacer arm (see FIG. 1) addition in presence of PB or IVIES buffer, 80 mM-200 mM, pH 5.8-6.2. Functionalized CRM197 was purified using 10-30 KD TFF cassettes (FIG. 2).

Example 4. Conjugation Process of Functionalized CRM197 to L1 VLP

The basic method steps of conjugation as follows:
1. Chemical conjugation between L1 or L2-VLPs and carrier protein CRM197 (FIG. 3).
2. Evaluation of HPV VLPs integrity after conjugation with CRM197.
3. Analytical characterization of HPV L1 and L2 VLPs and chemically conjugated bi-valent unimolecular or bi-valent VLPS.
4. Formulation of VLP-protein conjugates.
5. Comparison of Immunogenicity with Gardasil-9.
6. Stability study of VLP conjugates.

Examples of conjugates formed include:
I. Conjugation process of L116 HPV-VLP to functionalized CRM197.
II. Conjugation process of L1 HPV 1.6 VLP-CRM to L1-HPV 18 VLP (FIG. 4).
III. Conjugation process of L1 58 HPV-VLP-CRM197-L2 HPV VLP.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. An immunogenic composition comprising multivalent virus-like particles (VLPs) comprised of L1 or L2 proteins of Human papilloma virus (HPV) coupled to a heterobifunctional, homobifunctional, or multifunctional spacer arm which is coupled to a carrier protein, wherein the carrier protein is coupled to another a heterobifunctional, homobifunctional, or multifunctional spacer arm which is coupled to another L1 or L2 protein of HPV.

2. The immunogenic composition of claim 1, wherein the HPV comprises serotype 6, 11, 16, 18, 31, 33, 45, 52, and/or 58.

3. The immunogenic composition of claim 1, wherein at least one spacer arm comprises $NH_2$-PEG-$NH_2$/NHS, NHS/$NH_2$-PEG-COOH, Mal-PEG-$NH_2$, Mal-PEG-NHS, CHO-PEG-CHO, SH-PEG-$NH_2$, ADH, HZ-PEG-HZ, SMPH, SMCC, or 4-Arm-PEG-$NH_2$.

4. The immunogenic composition of claim 1, wherein the carrier protein comprises tetanus toxoid, diphtheria toxoid, CRM197, tetanus toxoid fragments (TTHc), *N. meningitidis* protein PorB, RSV virus proteins, *B. Pertussis* proteins, Pertussis toxoid (PT), adenylate cyclase toxin (ACT), 69 KDa protein, Human Papilloma viral protein antigens, Human Papilloma virus VLP forms, Hepatitis B virus core antigen, Hepatitis B virus VLP forms, derivatives of HBsAg, and/or combinations thereof.

5. The immunogenic composition of claim 1, further comprising an adjuvant.

6. The immunogenic composition of claim 5, wherein the adjuvant comprises aluminum salt, calcium phosphate, a liposome of monophosphoryl lipid A (MPLA), saponin QS-21, TLR ligands, and/or a potent TLR4/7/8/9 agonists.

7. The immunogenic composition of claim 6, wherein the aluminum salt is selected from the group consisting of aluminum phosphate, aluminum sulfate and/or aluminum hydroxide.

8. The immunogenic composition of claim 1, wherein the VLP is obtained or derived from HPV L1 protein and HPV L2 protein and the carrier protein is CRM197.

9. The immunogenic composition of claim 1, wherein the VLPs are bi-valent L1 VLP conjugates, the HPV is serotype 16 and/or 18, and the carrier protein is CRM197.

10. The immunogenic composition of claim 1, wherein the VLPs are bi-valent L1 VLP conjugates, the HPV is serotype 6 and/or 11, and the carrier protein is CRM197.

11. The immunogenic composition of claim 1, wherein the VLPs are bi-valent L1 VLP conjugates, the HPV is serotype 31 and/or 33, and the carrier protein is CRM197.

12. The immunogenic composition of claim 1, wherein the VLPs are bi-valent L1 VLP conjugates, the HPV is serotype 45 and/or 52, and the carrier protein is CRM197.

13. The immunogenic composition of claim 1, wherein the VLPs are bi-valent L1 VLP conjugates, the HPV is serotype 58, and the carrier protein is CRM197.

14. The immunogenic composition of claim 1, wherein the VLPs comprise L1 protein conjugated to L2 protein, and the carrier protein is CRM197.

15. The immunogenic composition of claim 1, wherein administration to a patient boosts the efficacy of a conventional vaccine.

16. An immunogenic composition comprising multivalent virus-like particles (VLPs) comprised of L1 protein of Human papilloma virus (HPV), coupled to a spacer arm which is coupled to a carrier protein and the carrier protein is coupled to another spacer arm which is coupled to another L1 or L2 protein of HPV, wherein:
the HPV comprises serotype 6, 11, 16, 18, 31, 33, 45, 52, and/or 58;
at least one spacer arm comprises a hetero-bifunctional spacer arm, which contains polyethylene glycol (PEG) and a hydrazide or modified hydrazide; and
the carrier protein comprises tetanus toxoid or diphtheria toxoid.

17. The immunogenic composition of claim 16, further comprising an adjuvant.

18. An immunogenic composition comprising multivalent virus-like particles (VLPs) comprised of L2 protein of Human papilloma virus (HPV), coupled to a spacer arm which is coupled to a carrier protein and the carrier protein is coupled to another spacer arm which is coupled to another L1 or L2 protein of HPV, wherein:
the HPV comprises serotype 6, 11, 16, 18, 31, 33, 45, 52, and/or 58;

at least one spacer arm comprises a hetero-bifunctional spacer arm, which contains polyethylene glycol (PEG) and a hydrazide or modified hydrazide; and the carrier protein comprises tetanus toxoid or diphtheria toxoid.

19. The immunogenic composition of claim 18, further comprising an adjuvant.

20. The immunogenic composition of claim 16, wherein at least one spacer arm comprises $NH_2$-PEG-$NH_2$/NHS, NHS/$NH_2$-PEG-COOH, Mal-PEG-$NH_2$, Mal-PEG-NHS, CHO-PEG-CHO, SH-PEG-$NH_2$, ADH, HZ-PEG-HZ, SMPH, SMCC, or 4-Arm-PEG-$NH_2$.

21. The immunogenic composition of claim 18, wherein each spacer arm comprises $NH_2$-PEG-$NH_2$/NHS, NHS/$NH_2$-PEG-COOH, Mal-PEG-$NH_2$, Mal-PEG-NHS, CHO-PEG-CHO, SH-PEG-$NH_2$, ADH, HZ-PEG-HZ, SMPH, SMCC, or 4-Arm-PEG-$NH_2$.

22. The immunogenic composition of claim 1, wherein upon administration to a patient of two doses at about 20-40 µg per dose generates a protective immune response against HPV.

23. The immunogenic composition of claim 16, wherein upon administration to a patient of two doses at about 20-40 µg per dose generates a protective immune response against HPV.

24. The immunogenic composition of claim 18, wherein upon administration to a patient of two doses at about 20-40 µg per dose generates a protective immune response against HPV.

25. The immunogenic composition of claim 1, wherein upon administration to a patient of two doses at about 8-10 µg per dose generates a protective immune response against HPV.

26. The immunogenic composition of claim 16, wherein upon administration to a patient of two doses at about 8-10 µg per dose generates a protective immune response against HPV.

27. The immunogenic composition of claim 18, wherein upon administration to a patient of two doses at about 8-10 µg per dose generates a protective immune response against HPV.

28. The immunogenic composition of claim 25, wherein a second dose is administered about two months after a first dose.

29. The immunogenic composition of claim 26, wherein a second dose is administered about two months after a first dose.

30. The immunogenic composition of claim 27, wherein a second dose is administered about two months after a first dose.

* * * * *